United States Patent [19]

Hussain

[11] Patent Number: 5,003,117

[45] Date of Patent: Mar. 26, 1991

[54] PROCESS FOR DECABROMODIPHENYL METHANE

[75] Inventor: Saadat Hussain, Baton Rouge, La.

[73] Assignee: Ethyl Corporation, Richmond, Va.

[21] Appl. No.: 389,521

[22] Filed: Aug. 3, 1989

[51] Int. Cl.$^5$ .................... C07C 17/12; C07C 25/18
[52] U.S. Cl. ................... 570/210; 570/206; 570/208
[58] Field of Search ............... 570/206, 208, 210

[56] References Cited

U.S. PATENT DOCUMENTS

| 4,072,658 | 2/1978 | Okamoto et al. | 260/49 |
| 4,287,373 | 9/1981 | Garman et al. | 568/639 |
| 4,521,633 | 6/1985 | Pedjac | 568/639 |

FOREIGN PATENT DOCUMENTS

| 708209 | 4/1965 | Canada | 570/206 |
| 0265150 | 4/1988 | European Pat. Off. | 568/637 |
| 2950877 | 6/1981 | Fed. Rep. of Germany | 570/206 |
| 52-39639 | 3/1977 | Japan | 570/206 |
| 53-116332 | 10/1978 | Japan | 570/206 |
| 53-116333 | 10/1978 | Japan | 570/206 |
| 53-116334 | 10/1978 | Japan | 570/206 |
| 56-70060 | 6/1981 | Japan . | |
| 1411524 | 10/1957 | United Kingdom | 570/206 |
| 981833 | 1/1965 | United Kingdom | 570/210 |
| 991067 | 5/1965 | United Kingdom | 570/210 |
| 1472383 | 5/1977 | United Kingdom | 568/637 |

Primary Examiner—Werren B. Lone
Attorney, Agent, or Firm—E. E. Spielman, Jr.; David E. LaRose

[57] ABSTRACT

This invention relates to process for preparing decabromodiphenyl methane, which process comprises: charging a reaction vessel with a first portion of a reaction solvent, a catalytic amount of a halogenation catalyst and from about 10 moles to about 30 moles of bromine per mole of diphenyl methane to be reacted; adding a solution of diphenyl methane and a second portion of the reaction solvent to the charged reaction vessel to form a reaction mass, the reaction mass, as it is being formed, being maintained at a temperature within the range of from about −15° C. to about 15° C.; after the diphenyl methane addition is substantially complete, maintaining the temperature of the reaction mass from about 50° C. to about 80° C.; and recovering from the reaction mass decabromodiphenyl methane.

7 Claims, No Drawings

PROCESS FOR DECABROMODIPHENYL METHANE

BACKGROUND OF THE INVENTION

This invention relates to a process for preparing decabromodiphenyl methane.

It is known that decabromodiphenyl oxide can be produced by reacting bromine and diphenyl oxide in the presence of a halogenation catalyst, e.g., anhydrous aluminum chloride. The reaction can be carried out by utilizing large stoichiometric excesses of bromine, say 20 moles of bromine per mole of diphenyl oxide, or by utilizing a slight stoichiometric excess of bromine and a reaction solvent, e.g., methylene chloride, methylene bromide, dibromoethane, dichloroethane, etc. In most commercial processes the reaction is initiated at 25° C. Since the reaction is exothermic and high reaction temperatures promote perbromination, the reaction temperature is usually allowed to rise to about 60° C. or higher.

It has been found that when such techniques are utilized in an attempt to prepare decabromodiphenyl methane from diphenyl methane and bromine that the yield of decabromodiphenyl methane is poor, i.e., less than 60 percent yield, due to production of undesirable by-products, such as hexabromobenzene, pentabromobenzyl bromide and bromoform. These unacceptable results are believed to be due to cleavage of the diphenyl methane at the benzyl carbon.

It is therefore an object of this invention to provide a process for producing decabromodiphenyl methane which is characterized by high yield, e.g., 95% yield, and insignificant cleavage of the diphenyl methane reactant.

THE INVENTION

In accordance with this invention, high yields of decabromodiphenyl methane are obtained by: charging a reaction vessel with a first portion of a reaction solvent, a catalytic amount of a halogenation catalyst and from about 13 moles to about 30 moles of bromine per mole of diphenyl methane to be reacted; adding a solution of diphenyl methane and a second portion of the reaction solvent to the charged reactor to form a stirrable reaction mass, the reaction mass, as it is being formed, being maintained at a temperature within the range of from about −5° C. to about 15° C.; after the diphenyl methane addition is substantially complete, maintaining the temperature of the reaction mass from about 50° C. to about 80° C. for from about 0.5 hours to about 5.0 hours; and recovering from the reaction mass decabromodiphenyl methane.

The diphenyl methane reactant is a commercially available compound and can be obtained from Aldrich Chemical Company, Inc. of Milwaukee, Wis.

The reaction solvent is a chlorinated or brominated aliphatic compound containing from 1 to 3 carbon atoms. The reaction solvent must be capable of solubilizing the diphenyl methane but not be necessarily an especially good solvent for decabromodiphenyl methane. The solvent must also be a liquid under process conditions. Exemplary of suitable solvents are dibromomethane, dichloromethane, bromochloromethane, dichloroethane, dibromoethane, chloroform, carbon tetrachloride, dibromochloroethane, etc. The most preferred solvents are dibromomethane, dichloromethane, dichloroethane, dibromoethane and mixtures thereof The reaction solvent is added in two portions. The first portion is used to dilute the bromine charged to the reaction vessel so that the diphenyl methane reactant is not exposed to a high concentration of bromine during its addition. The second portion of solvent is used to dissolve the diphenyl methane reactant so that it will be added as a dilute solution to the reaction vessel. The first portion will generally account for from about 20 percent to about 80 percent of the total reaction solvent used. In most cases the second portion can simply be that amount sufficient to dissolve the diphenyl methane and the first portion can be the remaining amount of reaction solvent to be used.

The total amount of reaction solvent used should not only provide for the foregoing two functions, but it should also render the reaction mass stirrable throughout the process. In most instances, from about 0.5 moles to about 2.5 moles of total reaction solvent per mole of diphenyl methane used will be suitable. Preferred total amounts of reaction solvent are within the range of from about 0.5 moles to about 1.5 moles per mole of diphenyl methane.

The halogenation catalyst is any of those types of catalysts which have been found useful in promoting the halogenation of aromatic moieties. Without a catalyst the reaction will be slow and thus not as attractive from a commercial standpoint. Suitable catalyst are the anhydrous halides of aluminum and iron, e.g., aluminum bromide, iron chloride, aluminum chloride, aluminum fluoride, etc. The metals, aluminum and iron, can also be used but care must be taken with their use as they are extremely active in bromine. Preferred is anhydrous aluminum chloride. The amount used is that amount which provides the catalytic effect sought. Generally, from about 0.001 mole to about 0.1 mole per mole of bromine charged to the reaction vessel is preferred. Preferred is from about 0.005 mole to about 0.01 per mole of bromine.

The amount of bromine charged to the reaction vessel is generally from about 30 percent to about 300 percent in excess of the stoichiometric amount. Since the product sought is decabrominated, the stoichiometric relationship is ten moles of bromine for each mole of diphenyl methane. A preferred amount of bromine is from about 90 percent to about 150 percent in excess of the stoichiometric amount.

As before noted, the diphenyl methane is added as a solute to the reaction vessel. The temperature of the bromine, catalyst and reaction solvent to which the diphenyl methane is added is at a temperature below 15° C., preferably from about −5° C. to about 10° C. at the initiation of the diphenyl methane addition. Addition temperature below −15° C. are not commercially desirable as the rate of reaction is slow. As the addition of the diphenyl methane continues the forming reaction mass is kept within these temperature limits. The rate of diphenyl methane solute addition is that rate at which the temperature requirement during the addition can be met with the equipment used.

After the addition of the diphenyl methane solution is at least substantially complete, the temperature of the reaction mass is increased to a temperature within the range of from about 50° C. to about 80° C., and preferably within the range of from about 65° C. to about 75° C. The reaction mass is maintained at such a temperature for from about 0.5 to about 5.0 hours. From about 0.5 to about 3.5 hours is preferred. Maintenance of the reaction mass at the elevated temperature for the period chosen is for the purpose of assuring and effecting perbromination of the diphenyl methane. It would normally be expected that the use of these temperatures and periods would cause cleavage at the benzyl carbon, but, it is a feature of this invention that such does not occur to any significant extent. It is theorized, though this invention is not limited by any theory, that the partial bromination which occurs during the diphenyl methane solution addition is at the ortho- and para- positions of the aromatic nuclei. With the bromine at these positions, it is believed that the benzyl carbon is somehow protected from cleaving influences during the perbromination portion of the process.

When bringing the temperature of the reaction mass from the diphenyl methane solution addition temperature to the 50° C. to 80° C. temperature, care should be taken to protect against the scorching or burning of solid material which may be stuck to the walls of the reaction vessel. This problem can be obviated by vigorous agitation of the reaction mass to keep the solids from staying stuck to the vessel walls or by raising the reaction mass temperature slowly to the 50° C. to 80° C. temperature range. The latter techniques is preferred. When using this preferred technique, the rate of rise in reaction mass temperature can be within the range of from about 5C.°/hour to about 60C.°/hour. Other rates, higher and lower, can be used if the sticking problem is found to be non-existent or insignificant.

During the addition and temperature maintenance steps the contents of the vessel are preferably agitated, such as by stirring.

The reaction pressure during the addition step and the temperature maintenance step is preferably atmospheric, there being no criticality attributable to the reaction pressure. It is desirable that the reaction pressure be such that the reaction mass will reach reflux between 50° C. and 80° C. as control of the reaction mass temperature is facilitated thereby.

After the 50° C. to 80° C. temperature period is complete the reaction mass is allowed to cool to, say, about 30° C. to about 50° C. Water is then added thereto to deactivate the catalyst.

Since the decabromodiphenyl methane product is essentially the only solid constituent (it forms as a precipitate) in the reaction mass, its recovery therefrom can be effected by any conventional solid-liquid separation technique, such as by filtration, centrifugation, evaporation of the liquid from the reaction mass, etc.

The recovered decabromodiphenyl methane is preferably washed with a solvent, such as methylene dichloride and toluene, and then dried. To further remove any impurities from the washed and dried decabromodiphenyl methane, it can be oven-aged at a temperature of from about 175° C. to about 225° C. for a period of from about 6 to about 24 hours.

The following examples illustrate some of the features of the process of this invention are not meant to be taken as limiting the invention scope.

EXAMPLE I

To a 500 mL resin kettle equipped with a mechanical stirrer, a reflux condenser, a thermometer, a temperature regulator and an addition funnel was charged 52 mL (1.0 moles) of $Br_2$, and 75 mL of $CH_2Br_2$. The contents of the kettle were then cooled to 3° C. After obtainment of this temperature, 1.1 g of $AlCl_3$ was added and the kettle contents were stirred. A solution comprised of 16.8 grams (0.1 mole) of diphenyl methane and 25 mL of $CH_2Br_2$ was added to the kettle over a period of twenty minutes. During this addition the kettle contents were kept at a temperature of 3°-6° C. After the addition was complete, the contents were slowly allowed to rise to room temperature (25° C.) over a period of about one hour. The kettle contents were then slowly heated to 60° C. at which an exotherm to 70° C. was noted. The gel broke to form a slurry, which was stirred at 70° C. with stirring for about one hour.

The reaction was then allowed to cool to 40° C. After cooling, water (200 mL) was added to the kettle to deactivate the $AlCl_3$ catalyst. Excess $Br_2/CH_2Br_2$ was distilled until the vapor head temperature reached 100° C. indicating complete removal of the $CH_2Br_2$ and bromine. After the distillation the vessel contents were filtered and washed with $H_2O$ (100 mL), followed by drying to obtain 90.5 grams of a crude decabromodiphenyl methane product which represents a 94.5% yield.

The dried product was washed with 60 mL of $CH_2Cl_2$ and 60 mL of toluene and dried at 125° C. for one hour. After drying, the product was oven aged at 200° C. for 24 hours. The oven aged product was white and weighed 83.5 grams. Its melting point was (Differential Scanning Colorimetry, i.e., DSC) 251°-254° C. and (capillary) 248°-252° C. The percent bromine (Schoniger) was 81.7% which compares against 83.5% theoretical. Gas chromatography (G.C.) gave a single peak and a purity, by area percent, of 98%. (The G.C. analysis was run with the precipitate in solution with hot $CH_2Br_2$.)

EXAMPLE II

This Example is not of this invention and illustrates an attempt to produce decabromodiphenyl methane with the use of a large excess of $Br_2$.

A 1-liter resin kettle, equipped with a mechanical stirrer, a thermometer, a reflux condenser and a water scrubber, was charged with bromine 800 g (5.0 moles) and 3.4 g of anhydrous $AlCl_3$. Molten diphenyl methane (42 g, 0.25 mole) was added over a period of one hour at 25°-40° C. After the addition was complete, the reaction mass was heated and stirred at reflux (60° C.) for 4 hours. The reaction mass was then cooled, water was charged and excess bromine was distilled off. The product was filtered, washed twice with 250 mL water and then dried at 100° C., followed by oven-aging at 200° C. for 18 hours. This gave 248.6 g of a dark tan product (104% yield), which melted at 218°-238° C. Also, significant amounts of a solid was seen to have sublimed during the oven-aging process. This solid appeared to be strong lachrymator. The bromine content of the product was 86.7%, theory is 83.5%. The product was also found to have contained 47,805 ppm of hydrolyzable bromide, which is indicative of aliphatic bromination. DSC showed the presence of at least two components in about a 60:40 ratio with melting point of about 180° C. and 260° C. respectively. The component with the 260° C. melting point was brominated diphenyl methane, the component melting at 180° C. was probably a brominated benzyl bromide (e.g., tetrabromobenzyl bromide). In addition, small amounts of hexabromobenzene, carbon tetrabromide and other cleavage products were also suspected to be present.

What is claimed is:

1. A process for producing, in high yield, a decabromodiphenyl methane product, which process comprises:

(a) charging a reaction vessel with a first portion of a reaction solvent, a catalytic amount of a halogenation catalyst and bromine;

(b) adding a solution of diphenyl methane and a second portion of the reaction solvent to the reaction vessel to form a reaction mass, the diphenyl methane solution containing from about 0.077 moles to about 0.025 moles of diphenyl methane per mole of bromine charged in (a) and the reaction mass, as it is being formed, being maintained at a temperature within the range of from about $-5°$ C. to about $15°$ C.;

(c) after the addition in (b) is at least substantially complete, maintaining the temperature of the reaction mass at a temperature within the range of from about $50°$ C. to about $80°$ C. until decabromodiphenyl methane is formed as a precipitate in the reaction mass; and (d) recovering the formed decabromodiphenyl methane from the reaction mass.

2. The process of claim 1 wherein the reaction solvent is selected from dibromothane, dichloromethane and mixtures thereof.

3. The process of claim 1 wherein the first portion of the reaction solvent comprises from about 20 to about 80 percent of the total reaction solvent.

4. The process of claim 1 wherein the amount of reaction solvent is within the range of form about 5 moles to about 20 moles per mole of diphenyl methane added in (b).

5. The process of claim 1 wherein the halogenation catalyst is $AlCl_3$.

6. The process of claim 1 wherein the temperature in (b) is within the range of from about $-5°$ to about $10°$ C.

7. A decabromodiphenyl methane predominant product containing impurities and at least about 95 weight percent decabromodiphenyl methane produce by the process of claim 1.

* * * * *

UNITED STATES PATENT AND TRADEMARK OFFICE
CERTIFICATE OF CORRECTION

PATENT NO. : 5,003,117

DATED : March 26, 1991

INVENTOR(S) : Saadat Hussain

It is certified that error appears in the above-identified patent and that said Letters Patent is hereby corrected as shown below:

Column 6, line 2 reads "dibromothane" and should read -- dibromoethane --.

Column 6, line 18 reads "produce" and should read -- produced --.

Signed and Sealed this

First Day of December, 1992

Attest:

DOUGLAS B. COMER

*Attesting Officer*  *Acting Commissioner of Patents and Trademarks*